US012569116B2

(12) United States Patent
Yumbe et al.

(10) Patent No.: US 12,569,116 B2
(45) Date of Patent: Mar. 10, 2026

(54) PROCESSOR DEVICE, OPERATION METHOD OF PROCESSOR DEVICE, NON-TRANSITORY COMPUTER READABLE MEDIUM, AND ENDOSCOPE SYSTEM FOR DISPLAYING MOVEMENT TRAJECTORY OF ENDOSCOPE

(71) Applicant: FUJIFILM Corporation, Tokyo (JP)

(72) Inventors: Hirona Yumbe, Kanagawa (JP); Shigetoshi Ishikawa, Kanagawa (JP); Akemi Oda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 319 days.

(21) Appl. No.: 18/317,089

(22) Filed: May 14, 2023

(65) Prior Publication Data

US 2023/0277036 A1 Sep. 7, 2023

Related U.S. Application Data

(63) Continuation of application No. PCT/JP2021/037522, filed on Oct. 11, 2021.

(30) Foreign Application Priority Data

Nov. 17, 2020 (JP) ................................. 2020-190900

(51) Int. Cl.
*A61B 1/00* (2006.01)
*G06T 7/00* (2017.01)
(52) U.S. Cl.
CPC .......... *A61B 1/0005* (2013.01); *A61B 1/0008* (2013.01); *G06T 7/00* (2013.01); *G06T 2207/10068* (2013.01)

(58) Field of Classification Search
None
See application file for complete search history.

(56) References Cited

U.S. PATENT DOCUMENTS 10,524,641 B2 * 1/2020 Prisco ...................... A61B 6/12
10,898,286 B2 * 1/2021 Srinivasan ............. A61B 34/30
(Continued)

FOREIGN PATENT DOCUMENTS

CN 103068294 4/2013
EP 2700351 2/2014
(Continued)

OTHER PUBLICATIONS

WO2013132880A1—Machine English translation (Year: 2013).*
(Continued)

*Primary Examiner* — Vu Le
(74) *Attorney, Agent, or Firm* — JCIPRNET

(57) ABSTRACT

A movement trajectory calculation unit calculates a movement trajectory indicating a trajectory along which an endoscope has moved, by using a movement state of the endoscope. From an endoscopic image obtained by the endoscope, a first recognition processing unit recognizes that a tip portion of the endoscope has reached a turn-back position and recognizes which of an outward path or a return path the movement trajectory corresponds to. A display control unit displays, on a display, a movement trajectory display screen that presents the movement trajectory separately for the outward path or the return path.

13 Claims, 8 Drawing Sheets

(56) References Cited

U.S. PATENT DOCUMENTS

| | | | |
|---|---|---|---|
| 11,529,197 B2 * | 12/2022 | Kronman ................ | A61B 34/20 |
| 2008/0303898 A1 * | 12/2008 | Nishimura ............. | G16H 40/63 |
| | | | 348/E7.085 |
| 2012/0287238 A1 | 11/2012 | Onishi et al. | |
| 2012/0289777 A1 * | 11/2012 | Chopra ................ | A61B 5/6852 |
| | | | 382/128 |
| 2014/0031625 A1 * | 1/2014 | Donhowe .......... | A61B 1/00009 |
| | | | 600/141 |
| 2014/0088357 A1 | 3/2014 | Kuma et al. | |
| 2017/0164869 A1 * | 6/2017 | Lee ........................ | A61B 34/20 |
| 2018/0110401 A1 | 4/2018 | Watanabe | |
| 2018/0114319 A1 | 4/2018 | Kono et al. | |
| 2019/0231444 A1 | 8/2019 | Tojo et al. | |
| 2019/0290108 A1 | 9/2019 | Nakamitsu et al. | |
| 2019/0298458 A1 | 10/2019 | Srinivasan et al. | |
| 2020/0078103 A1 * | 3/2020 | Duindam ................ | A61B 1/009 |
| 2020/0205904 A1 | 7/2020 | Chopra | |
| 2020/0294227 A1 | 9/2020 | Usuda | |
| 2021/0042925 A1 | 2/2021 | Usuda | |
| 2021/0106209 A1 | 4/2021 | Usuda | |

FOREIGN PATENT DOCUMENTS

| | | | | |
|---|---|---|---|---|
| JP | 2003093326 | 4/2003 | | |
| JP | 2020146202 | 9/2020 | | |
| WO | 2013132880 | 9/2013 | | |
| WO | WO-2015168066 A1 * | 11/2015 | ........... | G06T 3/4038 |
| WO | WO-2016135966 A1 * | 9/2016 | ............. | A61B 1/009 |
| WO | 2017002184 | 1/2017 | | |
| WO | 2017006404 | 1/2017 | | |
| WO | WO-2018116572 A1 * | 6/2018 | ........... | A61B 5/4255 |
| WO | 2019220848 | 11/2019 | | |
| WO | 2020017212 | 1/2020 | | |
| WO | WO-2020194472 A1 * | 10/2020 | ............... | G06T 7/70 |

OTHER PUBLICATIONS

WO2017002184A1—Machine English translation (Year: 2017).*
WO2020194472A1—Machine English translation (Year: 2020).*
WO-2016135966-A1_original_English machine translation (Year: 2016).*
WO-2020194472-A1_original_English machine translation (Year: 2020).*
WO-2018116572-A1_original_English machine translation (Year: 2018).*
"International Search Report (Form PCT/ISA/210) of PCT/JP2021/037522," mailed on Dec. 28, 2021, with English translation thereof, pp. 1-7.
"Written Opinion of the International Searching Authority (Form PCT/ISA/237) of PCT/JP2021/037522," mailed on Dec. 28, 2021, with English translation thereof, pp. 1-8.
"Office Action of Japan Counterpart Application", issued on Apr. 1, 2025, with English translation thereof, p. 1-p. 6.
"Search Report of Europe Counterpart Application", issued on Apr. 9, 2024, pp. 1-8.
"Office Action of China Counterpart Application", issued on Jun. 27, 2025, with English translation thereof, p. 1-p. 16.

* cited by examiner

FIG. 10A
FIG. 10B
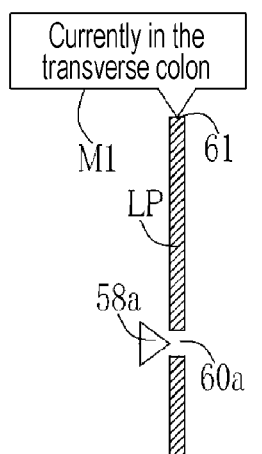
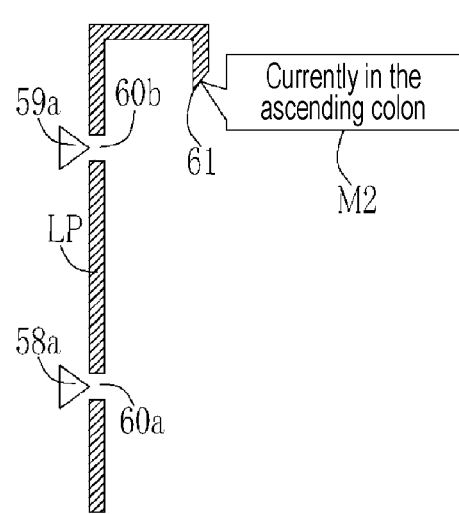
FIG. 11
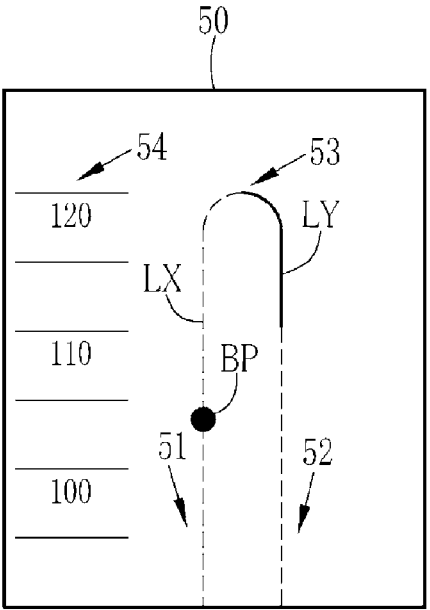

FIG. 14

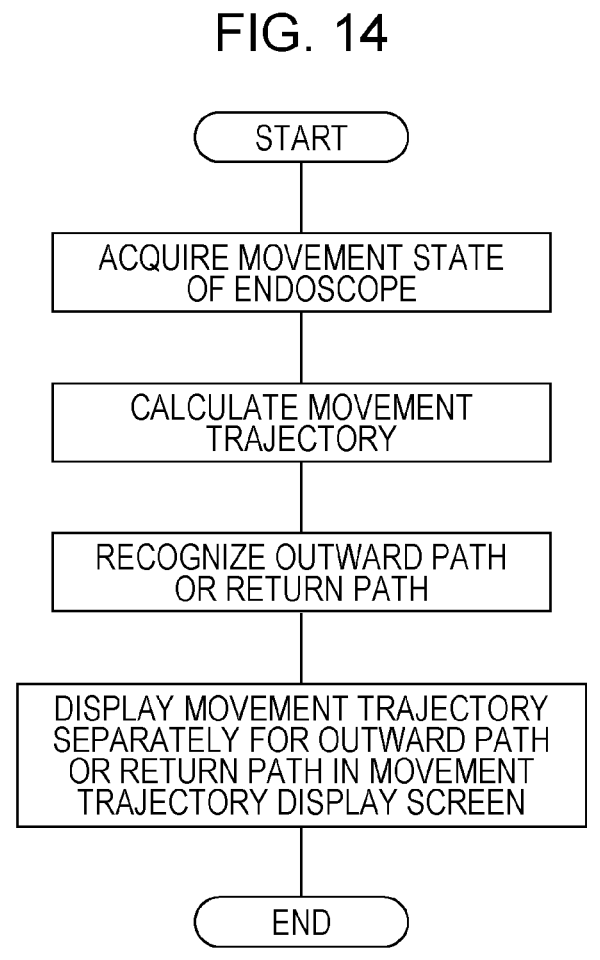

START

ACQUIRE MOVEMENT STATE
OF ENDOSCOPE

CALCULATE MOVEMENT
TRAJECTORY

RECOGNIZE OUTWARD PATH
OR RETURN PATH

DISPLAY MOVEMENT TRAJECTORY
SEPARATELY FOR OUTWARD PATH
OR RETURN PATH IN MOVEMENT
TRAJECTORY DISPLAY SCREEN

END

PROCESSOR DEVICE, OPERATION METHOD OF PROCESSOR DEVICE, NON-TRANSITORY COMPUTER READABLE MEDIUM, AND ENDOSCOPE SYSTEM FOR DISPLAYING MOVEMENT TRAJECTORY OF ENDOSCOPE

CROSS-REFERENCE TO RELATED APPLICATIONS

This application is a Continuation of PCT International Application No. PCT/JP2021/037522 filed on 11 Oct. 2021, which claims priority under 35 U.S.C § 119(a) to Japanese Patent Application No. 2020-190900 filed on 17 Nov. 2020. The above application is hereby expressly incorporated by reference, in its entirety, into the present application.

BACKGROUND OF THE INVENTION

1. Field of the Invention

The present invention relates to a processor device, an operation method of a processor device, a non-transitory computer readable medium, and an endoscope system in the case where a tip portion of an endoscope moves inside a body.

2. Description of the Related Art

In the current medical field, an endoscope system including a light source device, an endoscope, and a processor device is widely used. In the endoscope system, an endoscopic image obtained by the endoscope is displayed on a display, so that a state inside the body can be grasped. As described in JP2003-93326A, when an image of a current position is displayed on a display, a part corresponding to the current position is also displayed in a progress bar that indicates an inserted length. This makes it possible to grasp which position inside the body the image currently displayed on the display corresponds to.

SUMMARY OF THE INVENTION

In an endoscope system, when a digestive tract such as the stomach or the large intestine in the body is observed, a tip portion of an endoscope moves forward to and moves backward from a turn-back position. For example, when the large intestine is observed, the endoscope is inserted into the large intestine while being straightened or folded and is moved to the turn-back position. After the tip portion of the endoscope reaches the turn-back position, an operation of removing the endoscope is performed. Thus, the inserted length of the endoscope and the shape of the large intestine differ during insertion and removal of the endoscope. In this regard, the progress bar described in JP2003-93326A does not take into account the change in the shape of the large intestine or the like during insertion and removal, and thus has a difficulty in accurately displaying the current position.

An object of the present invention is to provide a processor device, an operation method of a processor device, a non-transitory computer readable medium, and an endoscope system that enable information on a current position to be accurately displayed in the case where a tip portion of an endoscope moves forward to and moves backward from a turn-back position inside a body.

According to the present invention, a processor device includes a processor configured to: acquire a movement state of an endoscope that moves inside a body; calculate a movement trajectory indicating a trajectory along which the endoscope has moved, by using the movement state of the endoscope; in a case where a tip portion of the endoscope moves forward to and moves backward from a turn-back position inside the body, from an endoscopic image obtained by the endoscope, recognize that the tip portion has reached the turn-back position and recognize which of an outward path or a return path the movement trajectory corresponds to; and display, on a display, a movement trajectory display screen that presents the movement trajectory separately for the outward path or the return path.

Preferably, an outward path display straight line that represents a movement trajectory of the outward path and a return path display straight line that represents a movement trajectory of the return path are displayed in the movement trajectory display screen. Preferably, the outward path display straight line and the return path display straight line are linked together by a turn-back display marking that represents the turn-back position. Preferably, an inserted length display scale that represents an inserted length of the endoscope is displayed for the outward path display straight line or the return path display straight line in the movement trajectory display screen. Preferably, an outward path display curved line that represents a movement trajectory of the outward path and a return path display curved line that represents a movement trajectory of the return path are displayed in the movement trajectory display screen.

Preferably, the processor is configured to: recognize a plurality of parts between an opening where the endoscope is inserted and the turn-back position, the plurality of parts including at least a first part and a second part; and classify the movement trajectory into a plurality of sections defined by the plurality of parts and display the plurality of sections in the movement trajectory display screen. Preferably, a section in which the tip portion is currently located is displayed with a message in the movement trajectory display screen.

Preferably, the processor is configured to: recognize a region of interest from the endoscopic image; and display a position of the region of interest on the movement trajectory in the movement trajectory display screen. Preferably, the processor is configured to: classify the region of interest into a category; and display, in the movement trajectory display screen, the position of the region of interest on the movement trajectory in a display style that changes depending on the category that is a result of the classification. Preferably, category information including the category of the region of interest is displayed for the movement trajectory in the movement trajectory display screen.

Preferably, the processor is configured to recognize a plurality of parts between an opening where the endoscope is inserted and the turn-back position, the plurality of parts including at least a first part and a second part, the plurality of parts define a plurality of sections, the movement trajectory is made up of a plurality of section movement trajectories provided for the respective sections, and section movement trajectory display screens that display the respective section movement trajectories are displayed in the movement trajectory display screen. Preferably, the movement state is a movement amount of the tip portion of the endoscope, and the movement amount of the tip portion is calculated based on at least an inserted length of the endoscope.

According to the present invention, an endoscope system includes a processor and a display, the processor being configured to: acquire a movement state of an endoscope that moves inside a body; calculate a movement trajectory indicating a trajectory along which the endoscope has moved, by using the movement state of the endoscope; in a case where a tip portion of the endoscope moves forward to and moves backward from a turn-back position inside the body, from an endoscopic image obtained by the endoscope, recognize that the tip portion has reached the turn-back position and recognize which of an outward path or a return path the movement trajectory corresponds to; and display, on the display, a movement trajectory display screen that presents the movement trajectory separately for the outward path or the return path.

According to the present invention, an operation method of a processor device including a processor, the operation method including: with the processor, acquiring a movement state of an endoscope that moves inside a body; calculating a movement trajectory indicating a trajectory along which the endoscope has moved, by using the movement state of the endoscope; in a case where a tip portion of the endoscope moves forward to and moves backward from a turn-back position inside the body, from an endoscopic image obtained by the endoscope, recognizing that the tip portion has reached the turn-back position and recognizing which of an outward path or a return path the movement trajectory corresponds to; and displaying, on a display, a movement trajectory display screen that presents the movement trajectory separately for the outward path or the return path.

According to the present invention, a non-transitory computer readable medium stores a computer-executable program that causes a computer to execute: a function of acquiring a movement state of an endoscope that moves inside a body; a function of calculating a movement trajectory indicating a trajectory along which the endoscope has moved, by using the movement state of the endoscope; a function of, in a case where a tip portion of the endoscope moves forward to and moves backward from a turn-back position inside the body, from an endoscopic image obtained by the endoscope, recognizing that the tip portion has reached the turn-back position and recognizing which of an outward path or a return path the movement trajectory corresponds to; and a function of displaying, on a display, a movement trajectory display screen that presents the movement trajectory separately for the outward path or the return path.

According to the present invention, information on a current position can be accurately displayed in the case where a tip portion of an endoscope moves forward to and moves backward from a turn-back position inside a body.

BRIEF DESCRIPTION OF THE DRAWINGS

FIG. 8 is a diagram illustrating a movement trajectory display screen that displays a movement trajectory as curved lines separately for an outward path and a return path;

FIGS. 9A, 9B, and 9C are explanatory diagrams each illustrating a movement trajectory classified into and displayed as three sections, that is, a movement trajectory of a current position, a moved movement trajectory, and a to-be-moved movement trajectory;

FIGS. 10A and 10B are explanatory diagrams each illustrating a movement trajectory classified into and displayed as two sections, that is, a movement trajectory of a current position and a moved movement trajectory;

FIG. 11 is a diagram illustrating a movement trajectory display screen that displays the movement trajectory as straight lines separately for an outward path and a return path and displays a position of a region of interest on the movement trajectory;

FIG. 14 is a flowchart illustrating a series of procedure steps of a movement trajectory display method.

DESCRIPTION OF THE PREFERRED EMBODIMENTS

Figure 1:
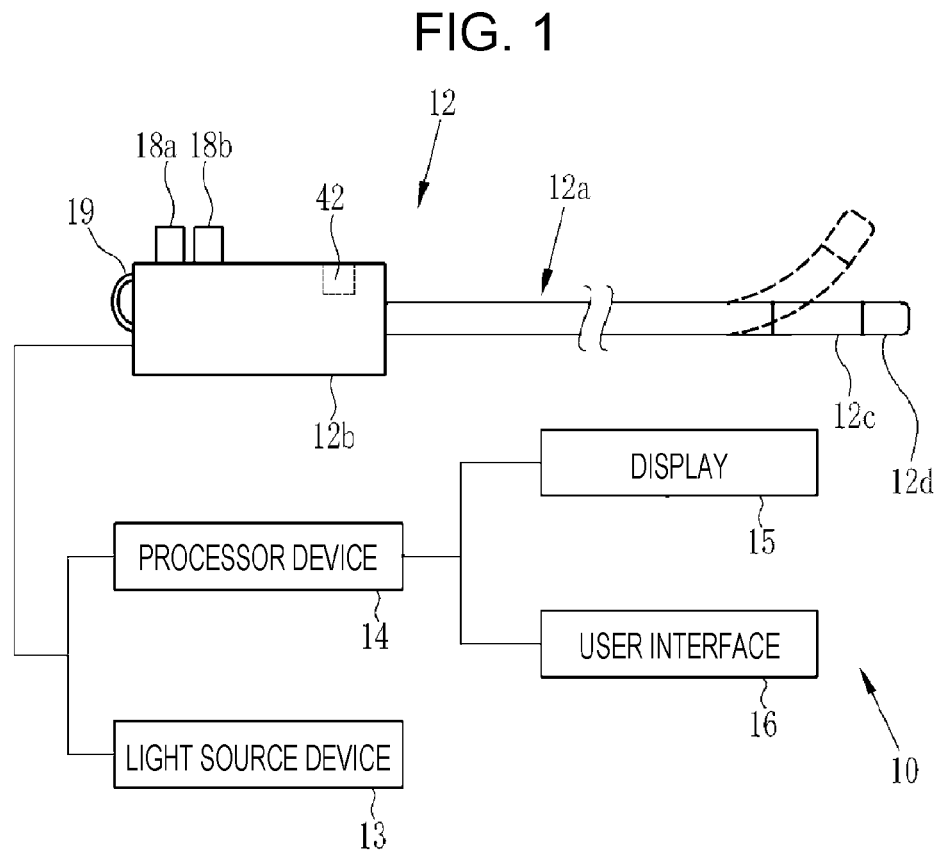
FIG. 1 is a schematic diagram of an endoscope system.

As illustrated in FIG. 1, an endoscope system 10 has an endoscope 12, a light source device 13, a processor device 14, a display 15, and a user interface 16. The endoscope 12 is optically connected to the light source device 13 and is electrically connected to the processor device 14. The endoscope 12 has an insertion section 12a to be inserted into a body of an observation target, an operation section 12b provided at a proximal end portion of the insertion section 12a, and a bending portion 12c and a tip portion 12d that are provided on a distal end side in the insertion section 12a. The bending portion 12c performs a bending action in response to an operation on the operation section 12b. The tip portion 12d is directed toward a desired direction by the bending action of the bending portion 12c.

The operation section 12b is provided with operation switches 18a and 18b used for various operations performed by a user. The operation switches 18a and 18b are assigned operation commands for performing the various operations via the user interface 16. The operation section 12b is provided with a zoom operation member 19 used for enlarging or reducing an image of the observation target.

The light source device 13 generates illumination light for illuminating the observation target, and supplies the generated illumination light to the endoscope 12. The endoscope 12 radiates the illumination light supplied from the light source device 13 toward the observation target, and images the observation target illuminated with the illumination light. The endoscope 12 sends, to the processor device 14, an endoscopic image obtained by imaging the observation target.

The processor device 14 is electrically connected to the display 15 and the user interface 16. The processor device 14 performs various kinds of image processing such as color tone adjustment processing or structure emphasis processing on the image obtained from the endoscope 12. The image on which the various kinds of image processing have been performed is sent to the display 15. The display 15 outputs, that is, displays an image of the observation target, information attached to the image of the observation target, and so on. The user interface 16 has a keyboard, a mouse, a touchpad, a microphone, or the like, and has a function of receiving an input operation for function setting or the like.

An expansion processor device (not illustrated) for performing artificial intelligence (AI)-based processing for detecting a lesion area using AI may be connected to the processor device 14. In this case, an expansion display (not illustrated) separate from the display 15 may be connected to the expansion processor device to display an image or the like processed by the expansion processor device. Thus, the "processor device" according to the present invention corresponds to the expansion processor device in addition to the processor device 14. Likewise, the "display" according to the present invention corresponds to the expansion display in addition to the display 15.

Figure 2:
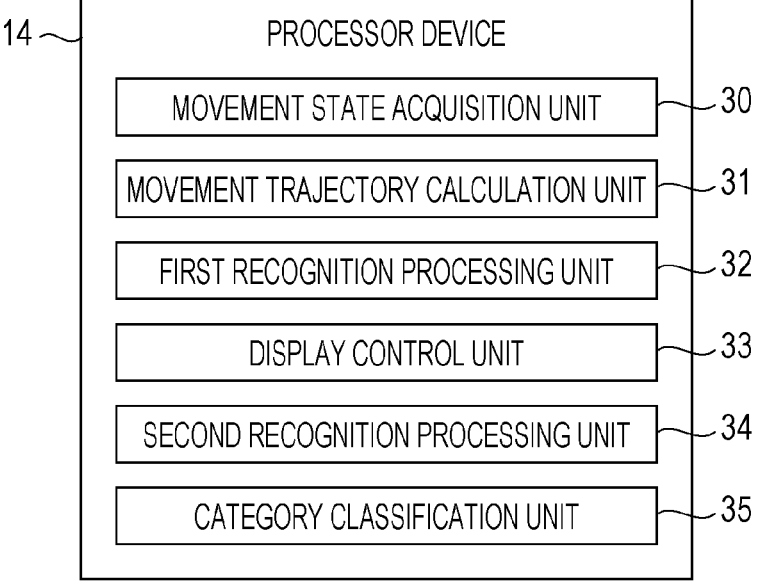
FIG. 2 is a block diagram illustrating functions of a processor device.

As illustrated in FIG. 2, the processor device 14 includes a movement state acquisition unit 30, a movement trajectory calculation unit 31, a first recognition processing unit 32, a display control unit 33, a second recognition processing unit 34, and a category classification unit 35. In the processor device 14, a program for the processor device (processor device program) for performing various kings of processing is installed in a program memory (not illustrated). The processor device 14 is provided with a central controller (not illustrated) constituted by a processor. The central controller executes the processor device program in the program memory to implement functions of the movement state acquisition unit 30, the movement trajectory calculation unit 31, the first recognition processing unit 32, the display control unit 33, the second recognition processing unit 34, and the category classification unit 35 described above.

Figure 3:
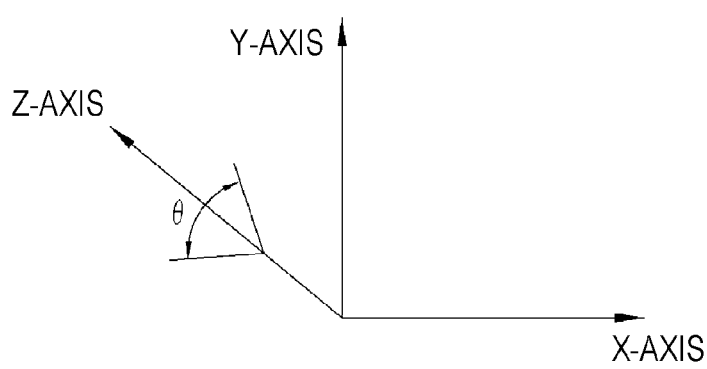
FIG. 3 is an explanatory diagram representing a moving direction of a tip portion of an endoscope.

The movement state acquisition unit 30 acquires a movement state of an endoscope that moves inside a body. Specifically, the movement state acquisition unit 30 preferably acquires the movement state, based on a movement amount of the tip portion 12*d* of the endoscope. As illustrated in FIG. 3, the movement amount of the tip portion 12*d* is preferably represented by a movement amount of the tip portion 12*d* in a left-right direction or an up-down direction (an X-axis direction or a Y-axis direction) and a rotation amount (θ (with a Z-axis as the center of rotation)) of the tip portion 12*d*, with respect to a moving direction (a Z-axis direction) of the tip portion 12*d* (by parameters X, Y, Z, and θ).

Figure 4:
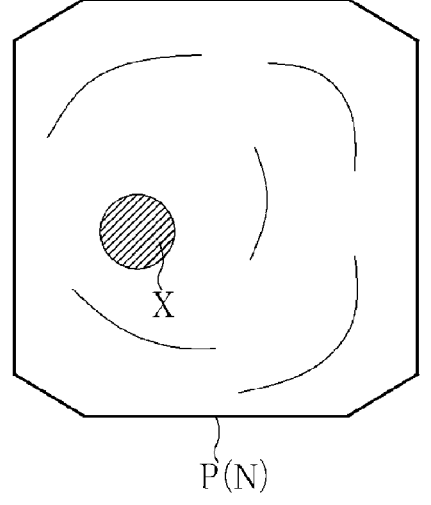
FIG. 4 is a diagram illustrating endoscopic images of two frames acquired at different timings.
Figure 4:
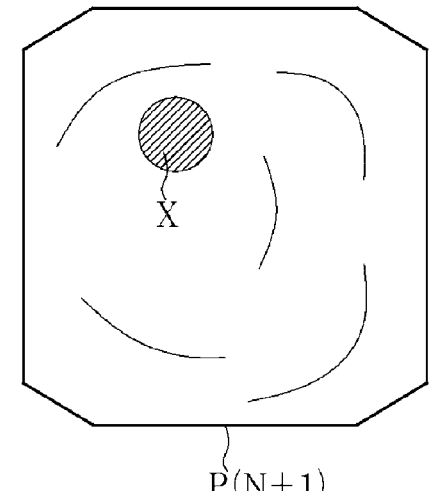

For example, as illustrated in FIG. 4, the movement state acquisition unit 30 preferably calculates the movement amount of the tip portion 12*d* through comparison between endoscopic images of at least two frames acquired by the endoscope at different timings (an endoscopic image P(N) of an N-th frame and an endoscopic image P(N+1) of an (N+1)-th frame). When the endoscopic image P(N) and P(N+1) are compared with each other, a region X is moved by a certain distance. In calculation of the movement amount of the tip portion 12*d* using endoscopic images, alignment processing between the endoscopic image P(N) and the endoscopic image P(N+1) is preferably used.

The alignment processing includes translation processing of translating the endoscopic image P(N) or the endoscopic image P(N+1) and enlargement/reduction processing of enlarging or reducing the endoscopic image P (N) or the endoscopic image P(N+1). The translation processing enables the movement amount of the tip portion 12*d* in the X-axis direction or the Y-axis direction and the rotation amount θ of the tip portion 12*d* about the Z-axis set as the center of rotation to be calculated. The enlargement/reduction processing enables the movement amount of the tip portion 12*d* in the moving direction Z at the time of insertion or removal to be calculated.

Figure 5:
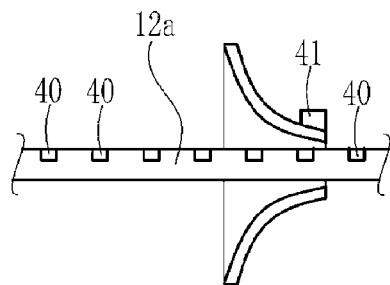
FIG. 5 is an explanatory diagram illustrating markers and a marker detection sensor for use in measuring an inserted length of the endoscope.

The movement state acquisition unit 30 may acquire the movement amount of the tip portion 12*d*, based on an inserted length of the insertion section 12*a* inserted into the body. In this case, as illustrated in FIG. 5, by using the insertion section 12*a* that is provided with markers 40 such as magnets disposed at certain intervals and by using a marker detection sensor 41 that detects the marker(s) 40 relative to an opening (an anus 44 (see FIG. 6) in the case where the inside of the body is the large intestine) where the endoscope 12 is inserted, the inserted length of the insertion section 12*a* is calculated based on a detection result of the marker(s) 40 obtained by the marker detection sensor 41 as the insertion section 12*a* moves (moves in the Z-axis direction). Note that the movement amount of the tip portion 12*d* in the X-axis direction or the Y-axis direction is preferably calculated using a movement amount measurement sensor 42 provided in the operation section 12*b*. The movement amount measurement sensor 42 calculates the movement amount of the tip portion 12*d* in the X-axis direction or the Y-axis direction from an amount of an operation on the bending portion 12*c*. Note that the movement amount of the tip portion 12*d* of the endoscope may be measured by a magnetic sensor such as an endoscope position detecting unit.

The movement trajectory calculation unit 31 calculates a movement trajectory indicating a trajectory along which the endoscope 12 has moved, by using the movement state of the endoscope 12. Specifically, the movement trajectory can be calculated by accumulating the movement state of the endoscope 12. In the case where the movement state of the endoscope 12 is represented by the movement amount (X, Y, Z, θ) of the tip portion 12*d*, the movement trajectory can be represented by a three-dimensional curved line by using all the four parameters (X, Y, Z, θ). The movement trajectory can also be represented as a two-dimensional curved line by performing projection processing on the three-dimensional curved line (see FIG. 8). By using only Z among the four parameters (X, Y, Z, θ), the movement trajectory can be represented by a straight line (see FIG. 7).

Figure 6:
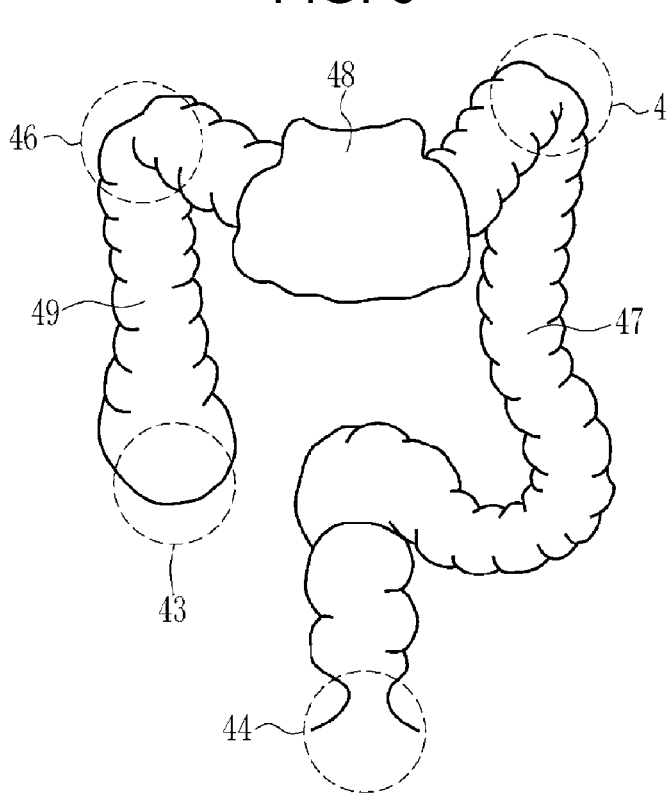
FIG. 6 is a schematic diagram of the large intestine.

In the case where the tip portion 12*d* of the endoscope moves forward to and moves backward from at a turn-back position in a body, from an endoscopic image obtained by the endoscope 12, the first recognition processing unit 32 recognizes that the tip portion 12*d* has reached the turn-back position and recognizes which of an outward path or a return path the movement trajectory corresponds to. Specifically, as illustrated in FIG. 6, in the case where the inside of the body is the large intestine, the turn-back position corresponds to an ileocecal region 43. The first recognition processing unit 32 performs processing of recognizing the ileocecal region 43 from an endoscopic image. Thus, until the first recognition processing unit 32 recognizes the ileocecal region 43 (when the ileocecal region 43 is not recognized), the first recognition processing unit 32 recognizes that the movement trajectory corresponds to the outward path. On the other hand, after the first recognition processing unit 32 recognizes the ileocecal region 43 (after the ileocecal region 43 is recognized), the first recognition processing unit 32 recognizes that the movement trajectory corresponds to the return path. Note that the first recognition processing unit 32 is preferably a trained model subjected to machine learning using endoscopic images serving as input images and respective correct answers (such as parts or positions).

The first recognition processing unit 32 also recognizes a plurality of parts between the opening where the endoscope 12 is inserted and the turn-back position. The plurality of parts includes at least a first part or a second part. Specifically, in the case where the inside of the body is the large intestine, the opening where the endoscope 12 is inserted corresponds to the anus 44, and the turn-back position corresponds to the ileocecal region 43. In addition, the first part on the anus side corresponds to a splenic flexure 45, and the second part on the ileocecal region side corresponds to a hepatic flexure 46. By recognizing the plurality of parts in this manner, a plurality of sections defined by the plurality of parts can be recognized. In the case where the inside of the body is the large intestine, three sections of a descending colon 47, a transverse colon 48, and an ascending colon 49 can be recognized by recognizing the splenic flexure 45 and the hepatic flexure 46.

If neither the splenic flexure 45 nor the hepatic flexure 46 is recognized, the first recognition processing unit 32 recognizes that the movement trajectory is in the section of the descending colon 47 in the outward path. If the splenic flexure 45 is recognized but the hepatic flexure 46 is not recognized, the first recognition processing unit 32 recognizes that the movement trajectory is in the section of the transverse colon 48 in the outward path. If the hepatic flexure 46 is recognized, the first recognition processing unit 32 recognizes that the movement trajectory is in the section of the ascending colon 49 in the outward path or the return path. If the hepatic flexure 46 is recognized and then the hepatic flexure 46 is recognized again, the first recognition processing unit 32 recognizes that the movement trajectory is in the section of the transverse colon 48 in the return path. If the hepatic flexure 46 is recognized and then the splenic flexure 45 is recognized, the first recognition processing unit 32 recognizes that the movement trajectory is in the section of the descending colon 47 in the return path.

Figure 7:
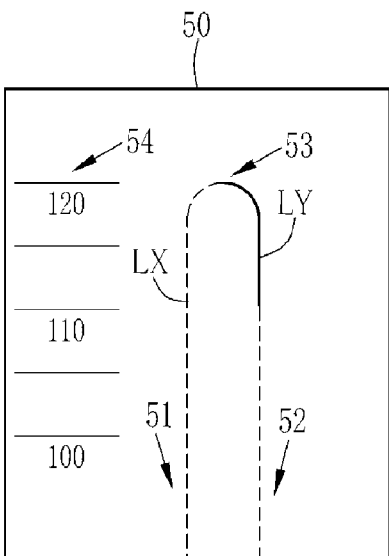
FIG. 7 is a diagram illustrating a movement trajectory display screen that displays a movement trajectory as straight lines separately for an outward path and a return path.

The display control unit 33 displays, on the display 15, a movement trajectory display screen that presents the movement trajectory separately for the outward path or the return path. Thus, the trajectory of the tip portion 12d is visualized separately for insertion (outward path) or removal (return path) of the endoscope 12. This can reduce an influence of a change in the shape of the inside of the body. Specifically, when the movement trajectory is represented as straight lines, the display control unit 33 displays, in a movement trajectory display screen 50, an outward path display straight line 51 that represents the movement trajectory of the outward path and a return path display straight line 52 that represents the movement trajectory of the return path as illustrated in FIG. 7.

In addition, the outward path display straight line 51 and the return path display straight line 52 are linked together by a turn-back display marking 53 that represents the turn-back position. The turn-back display marking 53 is semicircular but may have another shape (for example, a straight line (see FIG. 9A or the like)). Note that among the outward path display straight line 51, the return path display straight line 52, and the turn-back display marking 53, a solid line portion LY represents a position where the tip portion 12d is currently located, and a dash line portion LX represents a portion where the tip portion 12d has moved or a portion where the tip portion 12d is to move.

In addition, an inserted length display scale 54 that indicates the inserted length of the endoscope 12 may be displayed for the outward path display straight line 51 or the return path display straight line 52 in the movement trajectory display screen 50. The inserted length display scale 54 is preferably disposed beside the outward path display straight line 51 or the return path display straight line 52. The display of the inserted length display scale 54 is preferably switched (scrolled) to a scale corresponding to the actual inserted length as the tip portion 12d of the endoscope moves. For example, in the case of FIG. 7, since the tip portion 12d is near the turn-back position, the inserted length display scale 54 indicates an inserted length (100 cm to 120 cm) around the turn-back position. On the other hand, in the case where the tip portion 12d is in the section of the descending colon immediately after insertion, the inserted length display scale 54 indicates an inserted length of about 0 to 30 cm.

Figures 8, 9A, 9B, 9C:
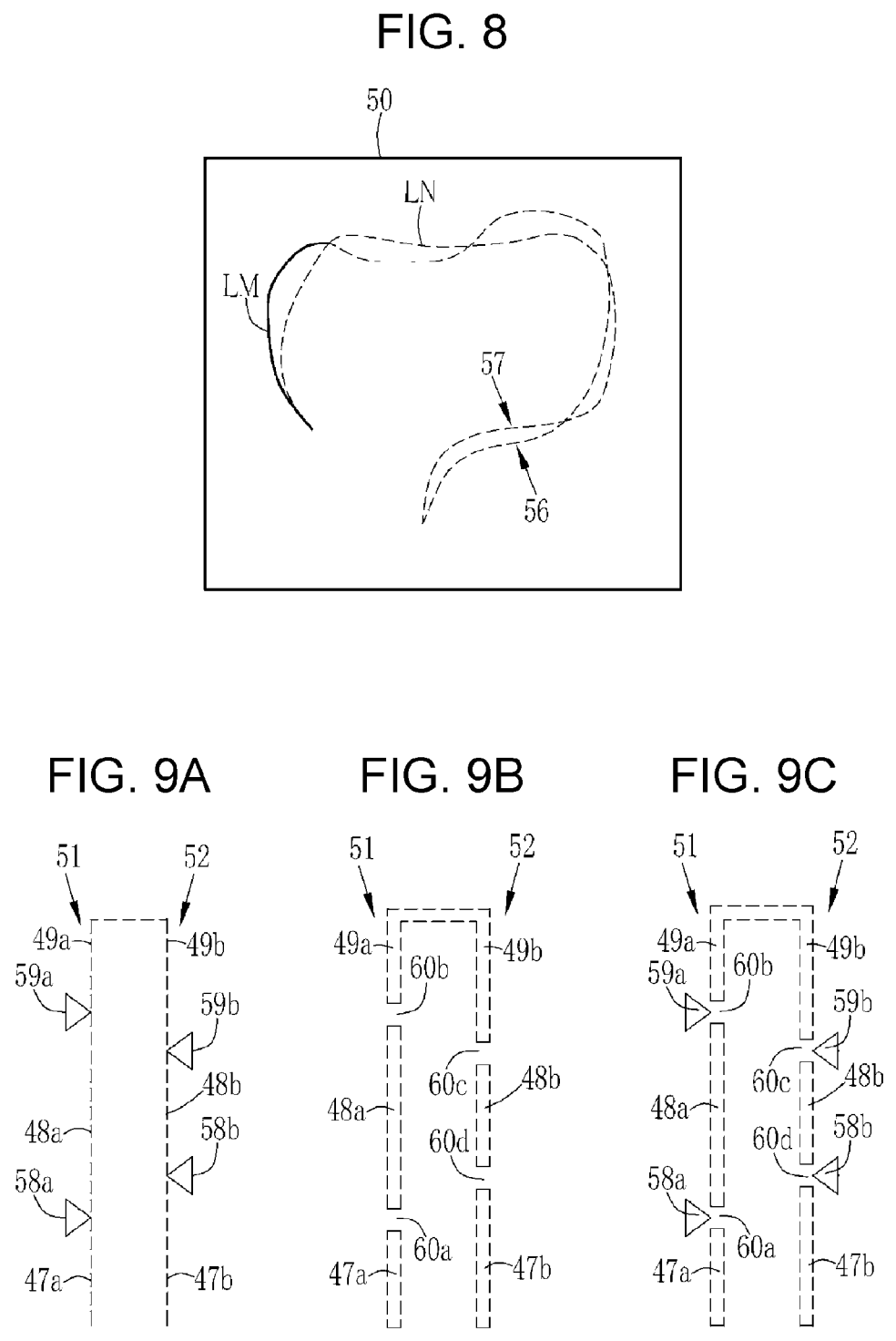

In the case where the movement trajectory is represented by a two-dimensional curved line, an outward path display curved line 56 that represents the movement trajectory of the outward path and a return path display curved line 57 that represents the movement trajectory of the return path are displayed in the movement trajectory display screen 50 as illustrated in FIG. 8. Note that among the outward path display curved line 56 and the return path display curved line 57, a solid line portion LM represents a position where the tip portion 12d is currently located, and a dash line portion LN represents a portion where the tip portion 12d has moved or a portion where the tip portion 12d is to move.

In addition, the movement trajectory may be classified into a plurality of sections defined by a plurality of parts and the plurality of sections may be displayed in the movement trajectory display screen 50. In the case where the inside of the body is the large intestine, the movement trajectory is preferably classified into three sections of the descending colon, the transverse colon, and the ascending colon defined by the splenic flexure (the first part) and the hepatic flexure (the second part) and displayed as the three sections. Specifically, in the case where the movement trajectory is represented by the outward path display straight line 51 or the return path display straight line 52, first part display markers 58a and 58b each representing the splenic flexure 45 and second part display markers 59a and 59b each representing the hepatic flexure 46 are used to represent a descending colon section 47a, a transverse colon section 48a, and an ascending colon section 49a in the outward path and represent a descending colon section 47b, a transverse colon section 48b, and an ascending colon section 49b in the return path as illustrated in FIG. 9A. Note that the descending colon sections 47a and 47b, the transverse colon sections 48a and 48b, and the ascending colon sections 49a and 49b described above are preferably displayed in different colors. Since the shape of the large intestine differs in the outward path and the return path, the first part display marker 58a and the second part display marker 59a on the outward path side and the first part display marker 58b and the second part display marker 59b on the return path side are displayed to be slightly shifted from each other on the straight lines.

As illustrated in FIG. 9B, instead of using the first part display markers 58a and 58b and the second part display markers 59a and 59b representing the hepatic flexure 46, breaks 60a, 60b, 60c, and 60d are preferably provided between the individual sections to make the descending colon section 47a, the transverse colon section 48a, and the ascending colon section 49a in the outward path and the descending colon section 47b, the transverse colon section 48b, and the ascending colon section 49b in the return path recognizable.

As illustrated in FIG. 9C, both of the set of the first part display markers 58a and 58b and the second part display markers 59a and 59b and the set of the breaks 60a, 60b, 60c, and 60*d* may be used to display the descending colon section 47*a,* the transverse colon section 48*a,* and the ascending colon section 49*a* in the outward path and the descending colon section 47*b,* the transverse colon section 48*b,* and the ascending colon section 49*b* in the return path to be recognizable.

Note that in FIG. 7 or 8, the position where the tip portion 12*d* of the endoscope is currently located is represented by the solid line portion LY or LM, and the portion where the tip portion 12*d* has moved or the portion where the tip portion 12*d* is to move is represented by the dash line portion LX or LN but may be represented by another method. For example, as illustrated in FIGS. 10A and 10B, in the movement trajectory display screen 50, only the current position of the tip portion 12*d* and the portion where the tip portion 12*d* has moved are represented by a solid line LP and the portion where the tip portion 12*d* is to move is not displayed. In this case, to display in which section the tip portion 12*d* is currently located, at least one of the set of the first part display markers 58*a* and 58*b* and the second part display markers 59*a* and 59*b* or the set of the breaks 60*a,* 60*b,* 60*c,* and 60*d* may be used to make the individual sections 47*a,* 47*b,* 48*a,* 48*b,* 49*a,* and 49*b* recognizable and the section in which the tip portion 12*d* is currently located may be indicated with a displayed message M1 or M2.

For example, FIG. 10A illustrates the movement trajectory at time t and the displayed message M1 indicates that the current position is "transverse colon". In addition, FIG. 10B illustrates the movement trajectory at time t+α after the time t, and the displayed message M2 indicates that the current position is the "ascending colon". The current position of the tip portion 12*d* of the endoscope is displayed as a tip-portion position 61 which is the distal end of the movement trajectory. When the tip portion 12*d* is located in the middle of each section, the tip-portion position 61 is displayed by cutting off part of the section. When the tip portion 12*d* is located at a boundary between the sections, the tip portion position 61 is displayed without the cut.

The second recognition processing unit 34 recognizes a region of interest from an endoscopic image. The region of interest is, for example, a region including a lesion area represented by cancer, a mark of treatment, a mark of surgery, a bleeding area, a benign tumor area, an inflammation area (including an area with a change such as bleeding or atrophy in addition to so-called inflammation), a mark of cauterization by heating, a marked area marked by coloration with a colorant or a fluorescent agent, or a biopsy performed area subjected to a biological examination (so-called biopsy). That is, a region including a lesion, a region that may be a lesion, a region subjected to some kind of treatment such as biopsy, a treatment tool such as a clip or forceps, a region that needs detailed observation regardless of the possibility of a lesion such as a dark region (a region to which observation light does not easily reach because the region is behind folds or deep in the lumen), or the like may be the region of interest. The second recognition processing unit 34 detects, as the region of interest, a region including at least any of a lesion area, a mark of treatment, a mark of surgery, a bleeding area, a benign tumor area, an inflammation area, a marked area, or a biopsy performed area. Note that similarly to the first recognition processing unit 32, the second recognition processing unit 34 is preferably a trained model subjected to machine learning using endoscopic images serving as input images and correct answers (such as presence or absence of a lesion).

The category classification unit 35 classifies the region of interest recognized by the second recognition processing unit 34 into a category. The category for classification is any of an imaged part, the presence or absence or type of a lesion which is one type of the region of interest, a use state of a treatment tool, a dispersion state of a coloring agent, and the like, or any combination thereof. Examples of the category of the region of interest include "hyper plastic (hyperplasia)", "neo plastic (tumor)", or the like.

As described above, in the case where a region of interest is recognized by the second recognition processing unit 34, the position of the region of interest is preferably displayed on the movement trajectory in the movement trajectory display screen 50. Specifically, in the case where the movement trajectory is represented by both the straight lines and the curved line, a region-of-interest detection point BP is displayed at a position where the region of interest is recognized, relative to the outward path display straight line 51, the return path display straight line 52, or the turn-back display marking 53 as illustrated in FIG. 11. In addition, the region-of-interest detection point BP is displayed at the position where the region of interest is recognized, relative to the outward path display curved line 56 or the return path display curved line 57.

Figure 12:
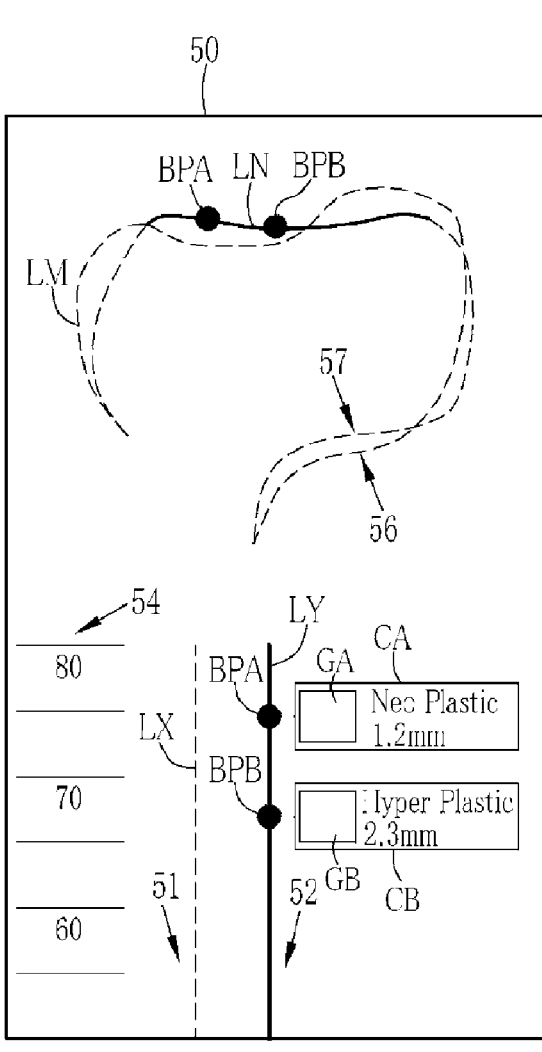
FIG. 12 is a diagram illustrating a movement trajectory display screen that displays the movement trajectory as straight lines and as curved lines separately for an outward path and a return path and displays positions of regions of interest on the movement trajectory.

In the case where the region of interest is classified into a category, the position of the region of interest may be displayed on the movement trajectory in the movement trajectory display screen 50 in a display style that changes depending on the category that is a result of the classification. Specifically, in the case where the movement trajectory is represented by both the straight lines and the curved lines, a region-of-interest detection point BPA for a category A is displayed at a position where a region of interest of the category A is recognized and a region-of-interest detection point BPB for a category B is displayed at a position where a region of interest of the category B (different from the category A) is recognized, relative to the outward path display straight line 51 or the return path display straight line 52 as illustrated in FIG. 12. For example, the color of the region-of-interest detection point BPA is preferably set to yellow, and the color of the region-of-interest detection point BPB is preferably set to green. In addition, the category A is, for example, "neo plastic", and the category B is, for example, "hyper plastic". Note that relative to the curved lines of the movement trajectory, display may be performed by using the region-of-interest detection points BPA and BPB having different display styles for different categories.

In addition, in the case where the region of interest is classified into a category, category information including the category of the region of interest may be displayed for the movement trajectory in the movement trajectory display screen 50. Specifically, in the outward path display straight line 51 or the return path display straight line 52, the region-of-interest detection point BPA for the category A is displayed at the position where the region of interest of the category A is recognized and category information CA including the category A of the region of interest and the size of the region of interest is displayed beside the region-of-interest detection point BPA. In addition, the region-of-interest detection point BPB for the category B is displayed at the position where the region of interest of the category B is recognized and category information CB including the category B of the region of interest and the size of the region of interest is displayed beside the region-of-interest detection point BPB. Note that the category information CA and the category information CB including images GA and GB of the regions of interest, respectively, may be displayed.

In the movement trajectory display screen 50, all the sections defined by the plurality of parts (for example, all the sections of the descending colon, the transverse colon, and the ascending colon in the case where the inside of the body is the large intestine) are displayed. However, in the case where an examination result is displayed after an examination ends such as in the case where a report is created using an endoscopic image, the movement trajectory may be made up of a plurality of section movement trajectories provided for the respective sections and section movement trajectory display screens displaying the respective section movement trajectories may be displayed in the movement trajectory display screen.

Figure 13:
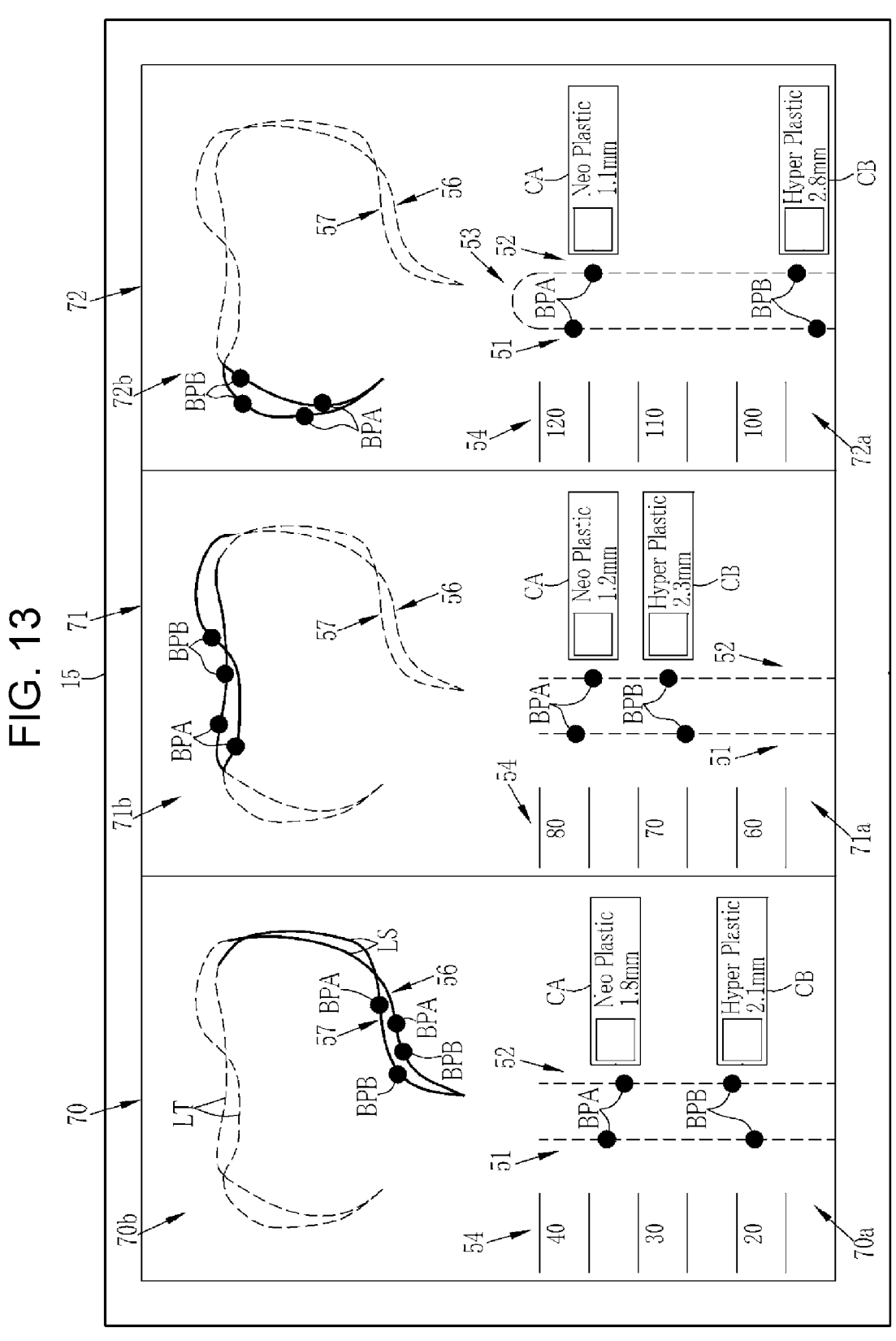
FIG. 13 is a diagram illustrating section movement trajectory display screens corresponding to three sections.

For example, in the case where the inside of the body is the large intestine and the splenic flexure (the first part) and the hepatic flexure (the second part) are recognized, the movement trajectory of the descending colon section is displayed in a section movement trajectory display screen 70, the movement trajectory of the transverse colon section is displayed in a section movement trajectory display screen 71, and the movement trajectory of the ascending colon section is displayed in a section movement trajectory display screen 72 as illustrated in FIG. 13. Dividing the movement trajectory into three sections and displaying the three sections reduce an amount of information on the movement trajectory or the region of interest per one display screen and thus improves a viewability for users. Note that when information on all the sections is displayed in a single screen, if the number of regions of interest is large, many markings (such as the region-of-interest detection point BPA) may be added to a single movement trajectory and may provide a poor viewability for users.

The section movement trajectory display screen 70 includes a straight line region 70a that represents the movement trajectory with straight lines and a curved line region 70b that represents the movement trajectory with curved lines. The straight line region 70a preferably displays only a portion where the region of interest is recognized in the movement trajectory. In addition, in the curved line region 70b, the descending colon section is represented by a solid line portion LS, and the other sections are represented by a dash line portion LT. The rest, such as the display method of the region of interest, is substantially the same as that in the above-described cases (see FIGS. 11 and 12).

Similarly to the section movement trajectory display screen 70, the section movement trajectory display screen 71 and the section movement trajectory display screen 72 also include straight line regions 71a and 72a and curved line regions 71b and 72b, respectively, and display the movement trajectory, the region of interest, or the like in substantially the same manner as in the section movement trajectory display screen 70.

Display of a movement trajectory will be described next with reference to a flowchart of FIG. 14. The movement state acquisition unit 30 provided in the processor device 14 acquires a movement state of an endoscope that moves inside a body. The movement trajectory calculation unit 31 calculates a movement trajectory indicating a trajectory along which the endoscope has moved, by using the movement state of the endoscope. The first recognition processing unit 32 recognizes, from an endoscopic image obtained by the endoscope 12, whether or not the tip portion 12d has reached the turn-back position.

If the first recognition processing unit 32 recognizes that the tip portion 12d has not reached the turn-back position, the first recognition processing unit 32 recognizes that the movement trajectory corresponds to the outward path. On the other hand, if the first recognition processing unit 32 recognizes that the tip portion 12d has reached the turn-back position, the first recognition processing unit 32 recognizes that the movement trajectory corresponds to the return path. The display control unit 33 displays, on the display 15, the movement trajectory display screen 50 that presents the movement trajectory separately for the outward path or the return path.

In the embodiment described above, a hardware structure of processing units that execute various processes, such as the movement state acquisition unit 30, the movement trajectory calculation unit 31, the first recognition processing unit 32, the display control unit 33, the second recognition processing unit 34, and the category classification unit 35, is implemented by processors mentioned below. The various processors include, for example, a central processing unit (CPU) or graphical processing unit (GPU) which is a general-purpose processor that executes software (program) to function as the various processing units; a programmable logic device (PLD) which is a processor whose circuit configuration is changeable after manufacture, such as a field programmable gate array (FPGA); and a dedicated electric circuitry which is a processor having a circuit configuration designed exclusively for executing the various processes.

One processing unit may be constituted by one of these various processors, or by a combination of two or more processors of the same kind or different kinds (for example, a plurality of FPGAs, a combination of a CPU and an FPGA, or a combination of a CPU and a GPU). In addition, a plurality of processing units may be constituted by a single processor. Examples in which the plurality of processing units are constituted by a single processor include a first configuration, as exemplified by computers such as a server and a client, in which a combination of one or more CPUs and software constitutes a single processor and this processor functions as the plurality of processing units. The examples also include a second configuration, as exemplified by a system on chip (SoC) or the like, in which a processor that implements the functions of the entire system including the plurality of processing units with a single integrated circuit (IC) chip is used. As described above, the various processing units are constituted by using one or more of the various processors described above in terms of the hardware structure.

Further, the hardware structure of these various processors is, more specifically, electric circuitry having a configuration in which circuit elements such as semiconductor elements are combined. In addition, the hardware structure of the storage unit is a storage device such as a hard disc drive (HDD) or a solid state drive (SSD).

REFERENCE SIGNS LIST 10 endoscope system
12 endoscope
12a insertion section
12b operation section
12c bending portion
12d tip portion
13 light source device
14 processor device
15 display
16 user interface
18a, 18b operation switch
19 zoom operation member
30 movement state acquisition unit
31 movement trajectory calculation unit
32 first recognition processing unit 33 display control unit
34 second recognition processing unit
35 category classification unit
40 marker
41 marker detection sensor
42 movement amount measurement sensor
43 ileocecal region
44 anus
45 splenic flexure
46 hepatic flexure
47 descending colon
47*a* descending colon section in outward path
47*b* descending colon section in return path
48 transverse colon
48*a* transverse colon section in outward path
48*b* transverse colon section in return path
49 ascending colon
49*a* ascending colon section in outward path
49*b* ascending colon section in return path
50 movement trajectory display screen
51 outward path display straight line
52 return path display straight line
53 turn-back display marking
54 inserted length display scale
56 outward path display curved line
57 return path display curved line
58*a*, 58*b* first part display marker
59*a*, 59*b* second part display marker
60*a*, 60*b*, 60*c*, 60*d* break
61 tip-portion position
70, 71, 72 section movement trajectory display screen
70*a*, 71*a*, 72*a* straight line region
70*b*, 71*b*, 72*b* curved line region
LY, LM, LS, LP solid line portion
LX, LN, LT dash line portion
M1, M2 message
BPA, BPB region-of-interest detection point
CA, CB category information
P(N), P(N+1) endoscopic image
GA, GB image of region of interest

What is claimed is:
1. A processor device comprising:
a processor configured to:
  acquire a movement state of an endoscope that moves inside a body;
  calculate a movement trajectory indicating a trajectory along which the endoscope has moved, by using the movement state of the endoscope;
  in a case where a tip portion of the endoscope moves forward to and moves backward from a turn-back position inside the body, from an endoscopic image obtained by the endoscope, recognize that the tip portion has reached the turn-back position and recognize which of an outward path or a return path the movement trajectory corresponds to; and
  display, on a display, a movement trajectory display screen that presents the movement trajectory separately for the outward path or the return path,
  wherein an outward path display straight line that represents a movement trajectory of the outward path and a return path display straight line that represents a movement trajectory of the return path are displayed in the movement trajectory display screen,
  wherein an inserted length display scale that represents an inserted length of the endoscope is displayed for the outward path display straight line or the return path display straight line in the movement trajectory display screen, and the inserted length display scale is disposed beside the outward path display straight line or the return path display straight line.

2. The processor device according to claim 1, wherein the outward path display straight line and the return path display straight line are linked together by a turn-back display marking that represents the turn-back position.

3. The processor device according to claim 1, wherein an outward path display curved line that represents a movement trajectory of the outward path and a return path display curved line that represents a movement trajectory of the return path are displayed in the movement trajectory display screen.

4. The processor device according to claim 1, wherein the processor is configured to:
  recognize a plurality of parts between an opening where the endoscope is inserted and the turn-back position, the plurality of parts including at least a first part and a second part; and
  classify the movement trajectory into a plurality of sections defined by the plurality of parts and display the plurality of sections in the movement trajectory display screen.

5. The processor device according to claim 4, wherein a section in which the tip portion is currently located is displayed with a message in the movement trajectory display screen.

6. The processor device according to claim 1, wherein the processor is configured to:
  recognize a region of interest from the endoscopic image; and
  display a position of the region of interest on the movement trajectory in the movement trajectory display screen.

7. The processor device according to claim 6, wherein the processor is configured to:
  classify the region of interest into a category; and
  display, in the movement trajectory display screen, the position of the region of interest on the movement trajectory in a display style that changes depending on the category that is a result of the classification.

8. The processor device according to claim 7, wherein category information including the category of the region of interest is displayed for the movement trajectory in the movement trajectory display screen.

9. The processor device according to claim 1, wherein
  the processor is configured to recognize a plurality of parts between an opening where the endoscope is inserted and the turn-back position, the plurality of parts including at least a first part and a second part,
  the plurality of parts define a plurality of sections,
  the movement trajectory is made up of a plurality of section movement trajectories provided for the respective sections, and
  section movement trajectory display screens that display the respective section movement trajectories are displayed in the movement trajectory display screen.

10. The processor device according to claim 1, wherein
  the movement state is a movement amount of the tip portion of the endoscope, and
  the movement amount of the tip portion is calculated based on at least an inserted length of the endoscope.

11. An endoscope system comprising:

a processor; and a display, the processor being configured to:

acquire a movement state of an endoscope that moves inside a body;

calculate a movement trajectory indicating a trajectory along which the endoscope has moved, by using the movement state of the endoscope;

in a case where a tip portion of the endoscope moves forward to and moves backward from a turn-back position inside the body, from an endoscopic image obtained by the endoscope, recognize that the tip portion has reached the turn-back position and recognize which of an outward path or a return path the movement trajectory corresponds to; and display, on the display, a movement trajectory display screen that presents the movement trajectory separately for the outward path or the return path, wherein an outward path display straight line that represents a movement trajectory of the outward path and a return path display straight line that represents a movement trajectory of the return path are displayed in the movement trajectory display screen, wherein an inserted length display scale that represents an inserted length of the endoscope is displayed for the outward path display straight line or the return path display straight line in the movement trajectory display screen, and the inserted length display scale is disposed beside the outward path display straight line or the return path display straight line.

12. An operation method of a processor device including a processor, the operation method comprising steps, performed by the processor, of:

acquiring a movement state of an endoscope that moves inside a body;

calculating a movement trajectory indicating a trajectory along which the endoscope has moved, by using the movement state of the endoscope;

in a case where a tip portion of the endoscope moves forward to and moves backward from a turn-back position inside the body, from an endoscopic image obtained by the endoscope, recognizing that the tip portion has reached the turn-back position and recognizing which of an outward path or a return path the movement trajectory corresponds to; and displaying, on a display, a movement trajectory display screen that presents the movement trajectory separately for the outward path or the return path, wherein an outward path display straight line that represents a movement trajectory of the outward path and a return path display straight line that represents a movement trajectory of the return path are displayed in the movement trajectory display screen, wherein an inserted length display scale that represents an inserted length of the endoscope is displayed for the outward path display straight line or the return path display straight line in the movement trajectory display screen, and the inserted length display scale is disposed beside the outward path display straight line or the return path display straight line.

13. A non-transitory computer readable medium for storing a computer-executable program for causing a computer to function as a processor device, the computer-executable program causing a computer to execute:

a function of acquiring a movement state of an endoscope that moves inside a body;

a function of calculating a movement trajectory indicating a trajectory along which the endoscope has moved, by using the movement state of the endoscope;

a function of, in a case where a tip portion of the endoscope moves forward to and moves backward from a turn-back position inside the body, from an endoscopic image obtained by the endoscope, recognizing that the tip portion has reached the turn-back position and recognizing which of an outward path or a return path the movement trajectory corresponds to; and a function of displaying, on a display, a movement trajectory display screen that presents the movement trajectory separately for the outward path or the return path, wherein an outward path display straight line that represents a movement trajectory of the outward path and a return path display straight line that represents a movement trajectory of the return path are displayed in the movement trajectory display screen, wherein an inserted length display scale that represents an inserted length of the endoscope is displayed for the outward path display straight line or the return path display straight line in the movement trajectory display screen, and the inserted length display scale is disposed beside the outward path display straight line or the return path display straight line.

* * * * *